United States Patent [19]
Kobayashi

[11] Patent Number: 4,755,873
[45] Date of Patent: Jul. 5, 1988

[54] ENDOSCOPE SYSTEM

[75] Inventor: Kazunari Kobayashi, Tokyo, Japan

[73] Assignee: Olympus Optical Co., Ltd., Tokyo, Japan

[21] Appl. No.: 46,295

[22] Filed: May 4, 1987

[30] Foreign Application Priority Data

May 14, 1986 [JP] Japan .............................. 61-109751

[51] Int. Cl.⁴ ............................................ H04N 7/18
[52] U.S. Cl. ............................................ 358/98; 128/6
[58] Field of Search ........................ 358/98, 224, 181; 128/6

[56] References Cited

U.S. PATENT DOCUMENTS 4,601,284 7/1986 Arakawa et al. ................. 358/98 X
4,641,635 2/1987 Yabe .................................. 358/98 X
4,651,202 3/1987 Arakawa ............................... 358/98

FOREIGN PATENT DOCUMENTS 61-208022 9/1986 Japan .

Primary Examiner—Howard W. Britton
Assistant Examiner—Victor R. Kostak
Attorney, Agent, or Firm—Frishauf, Holtz, Goodman & Woodward

[57] ABSTRACT

The present invention relates to an endoscope system which comprises an endoscope having a handy-control section and an insertion section adapted to be inserted into the body cavity, and a video-signal processing unit having an electric circuit capable of receiving and processing a video signal, produced by a solid-state image sensing device, through the medium of the endoscope, and of recording and/or displaying the video signal on a monitor TV. A receptacle, which is provided on the outer surface of the video-signal processing unit, includes an electrical connecting portion connected to the electric circuit in the processing unit. The endoscope system further comprises a video camera which has a solid-state image sensing device therein, and is mounted on an eyepiece portion for optical observation at the control section of the endoscope. The video camera is connected to a signal cord which has a plug connectable with the electrical connecting portion of the receptacle. Also, the video camera has remote control switches which can be used to control the video-signal processing unit through the medium of the signal cord. An operator can freely start recording or other operations by operating the remote control switches.

9 Claims, 4 Drawing Sheets

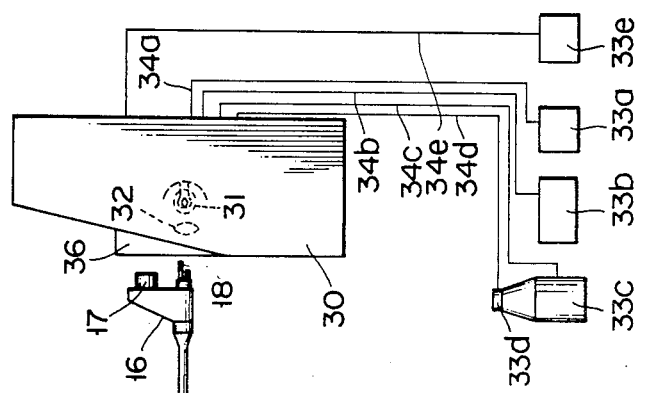
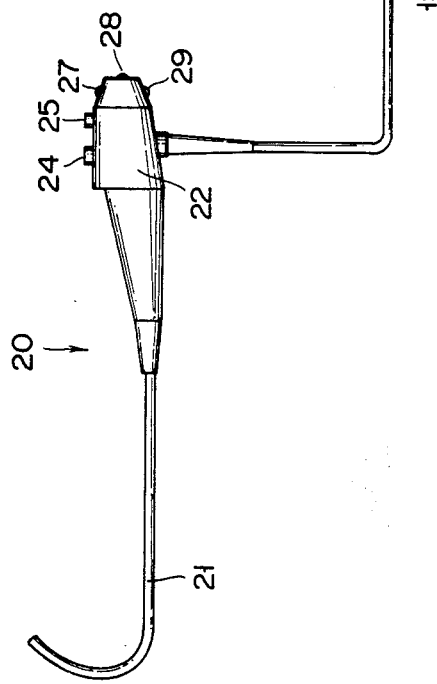
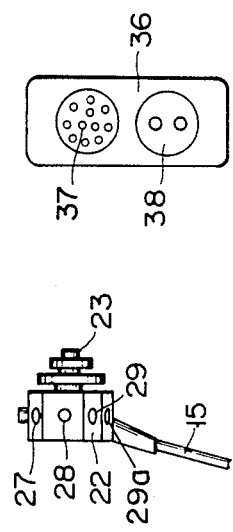
FIG. 1
FIG. 2
FIG. 3

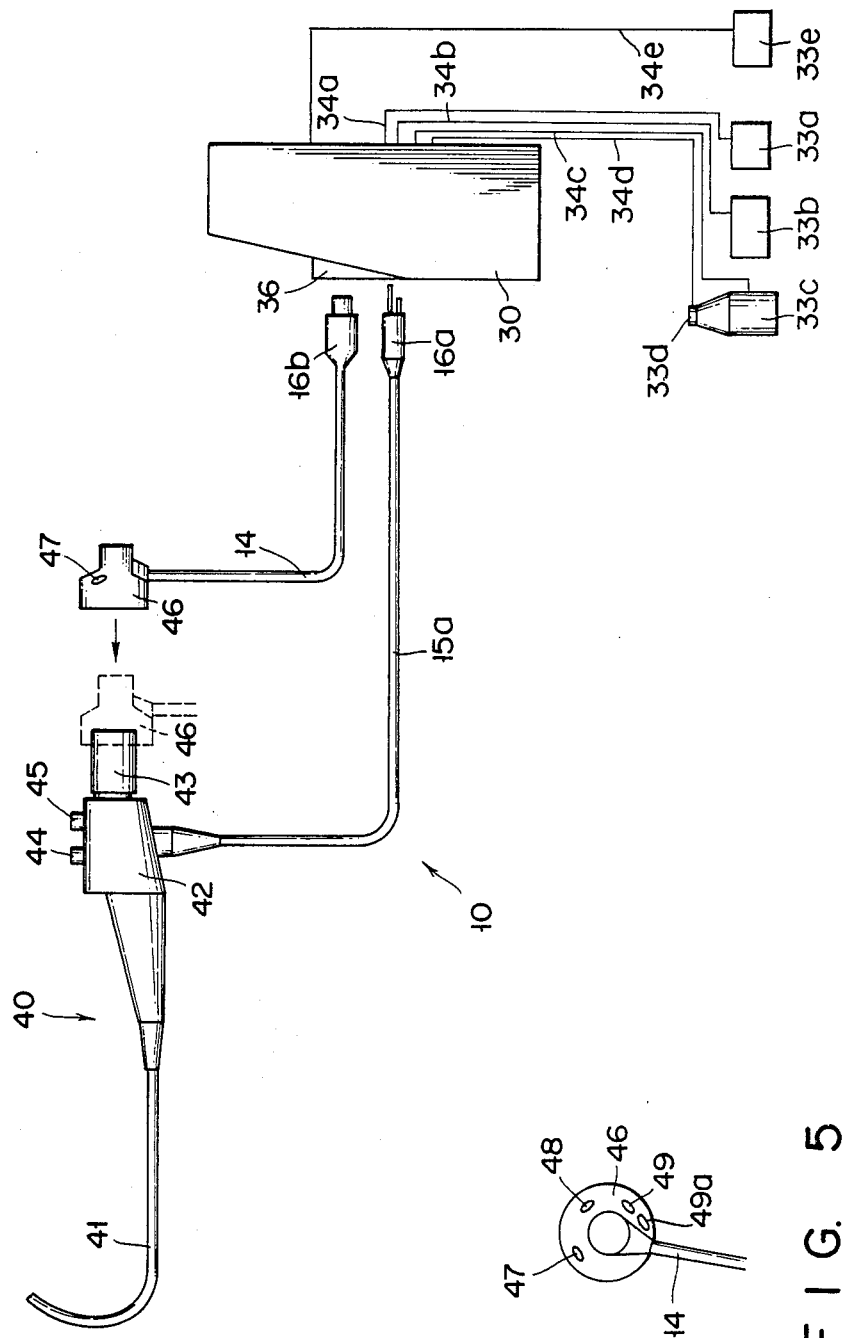

ENDOSCOPE SYSTEM

BACKGROUND OF THE INVENTION

The present invention relates to an endoscope system for processing a video signal formed by means of a solid-state image sensing device, and then displaying the processed signal on a screen of a monitor television or the like, for observation.

Endoscopes of various types are conventionally used in endoscope systems which are designed so that an insertion section is inserted into the human body cavity for observation of the inner body wall. Optical endoscopes, i.e., the so-called fiberscopes, have hitherto been used more frequently than endoscopes of any other types. The fiberscopes comprise a slender, flexible insertion section, which is adapted to be inserted into the body cavity, and a handy-control section coupled to the insertion section. As is generally known, the distal end portion of the insertion section is provided with an objective lens, a light guide and an image guide, each formed of a bundle of fibers, a waterfeed/suction port, a suction/forceps port, etc. The tilt angle of the distal end portion is adjustable. The control section includes control means for controlling gas or water feed, and adjusting means for angle adjustment of the distal end portion. According to these fiber scopes, the insertion section is inserted into the body cavity, and an optical image of a desired region, formed by the objective lens, is guided through the image guide to an eyepiece portion of the control section. The condition of the inner wall of the body cavity can be observed macroscopically through an optical lens at the eyepiece portion. The light guide is connected to a light source, and serves to illuminate the body wall for a clear view.

A novel technology has recently been developed in the field. According to this method, a video camera is mounted on the eyepiece portion of the optical endoscope, and a video signal, produced by a solid-state image sensing device of the camera, is transmitted to a video-signal processing unit. The signal received by the processing unit is processed thereby, and the condition of the desired region of the body wall is displayed on a monitor television or is recorded by means of a recorder. The on-off control of the recording operation and the like are performed by operating control switches on the recorder, which is situated at a distance from the fiber scope. The control switches should be operated by an assistant.

In a known endoscope of another type, a solid-state image sensing device is provided directly on the distal end of its insertion section. This endoscope is of an electronic-observation type, constructed so that the desired region of the inner body wall is illuminated with a light from a light source, guided through a light guide at the distal end portion of the insertion section. A video signal produced by the image sensing device, receiving the reflected light from the body wall, is transmitted to a video-signal processing unit. The processing unit can process the received video signal, and reproduce it on a monitor television or record it by means of a recorder. This electronic endoscope, unlike the fiberscope, is not adapted for macroscopic observation of the optical image which is indicative of the body wall. In the electronic endoscope, moreover, the on-off control of the recording operation and the like can be performed by operating control switches arranged on the side of the recorder. Also, an operator himself can execute the control by operating remote control switches, which are mounted on the handy-control section of the endoscope.

When using the optical endoscope with the video camera on the eyepiece portion of its handy-control section, the operator must operate the control switches on the recorder, remote from the endoscope, in order to effect the necessary operations, such as recording. Such a switching operation is very troublesome for the operator who is in charge of a medical examination. When the assistant operates the switches under instructions from the operator, there would inevitably be an time lag between the instructions and the operations by the assistant. In such a situation, it is very difficult for the operator to record a desired image of a desired region of the inner body wall.

When using the electronic endoscope, on the other hand, the operator himself can directly operate the control switches at the handy-control section, so that he can record his desired image with ease.

In most cases, the endoscopes of the two types, electronic and optical, are used alternatively at the request of one and the same operator.

However, the control switches are mounted on the handy-control section in the case of the electronic endoscope, and on the side of the recorder in the case of the optical endoscope with the video camera on its eyepiece portion. When alternately using the endoscopes of these two types, therefore, there is a difference in switching capability between the endoscopes which are used similarly with a monitor television for observation. Thus, the operator may get confused while operating the switches, thereby lowering the operating capability of the endoscope system.

SUMMARY OF THE INVENTION

An object of the present invention is to settle these problems of the prior art endoscope systems.

Another object of the invention is to provide an endoscope system which is constructed so that the operator can perform an accurate operation of control switches easily and quickly, without confusion, when using the system alternately with an electronic endoscope and an optical endoscope fitted with a video camera.

Still another object of the invention is to provide an endoscope system comprising a video-signal processing unit which has a receptacle connectable with both an electronic endoscope and an optical endoscope with a video camera mounted on its eyepiece portion.

In order to achieve the above objects, according to an endoscope system of the present invention, a receptacle, which is provided on the outer surface of a video-signal processing unit, includes an electrical connecting portion connected to an electric circuit in the processing unit. Further, the endoscope system comprises a video camera which has a solid-state image sensing device therein, and is mounted on an eyepiece portion for optical observation at a handy-control section of an endoscope. The video camera is connected to one end of a signal cord which has a plug connectable with the electrical connecting portion of the receptacle. Also, the camera has remote control switches which can be used to control the video-signal processing unit through the medium of the signal cord.

The operator can freely start recording or other operations by operating the remote control switches.

The above and other objects, features and advantages of the present invention will be apparent in the following detailed description of illustrative embodiments thereof which is to be read in connection with the accompanying drawings.

BRIEF DESCRIPTION OF THE DRAWINGS

FIG. 1 schematically shows an endoscope system using an electronic endoscope coupled to a video-signal processing unit;

FIG. 2 schematically shows the rear face of the electronic endoscope of FIG. 1;

FIG. 3 schematically shows a front portion of a receptacle located on the outer surface of the video-signal processing unit of FIG. 1;

FIG. 4 schematically shows an outline of an endoscope system using an optical endoscope with a video camera mounted on its eyepiece portion;

FIG. 5 schematically shows the rear face of a video camera shown in FIG. 4;

DETAILED DESCRIPTION OF THE PREFERRED EMBODIMENTS

Figure 6:
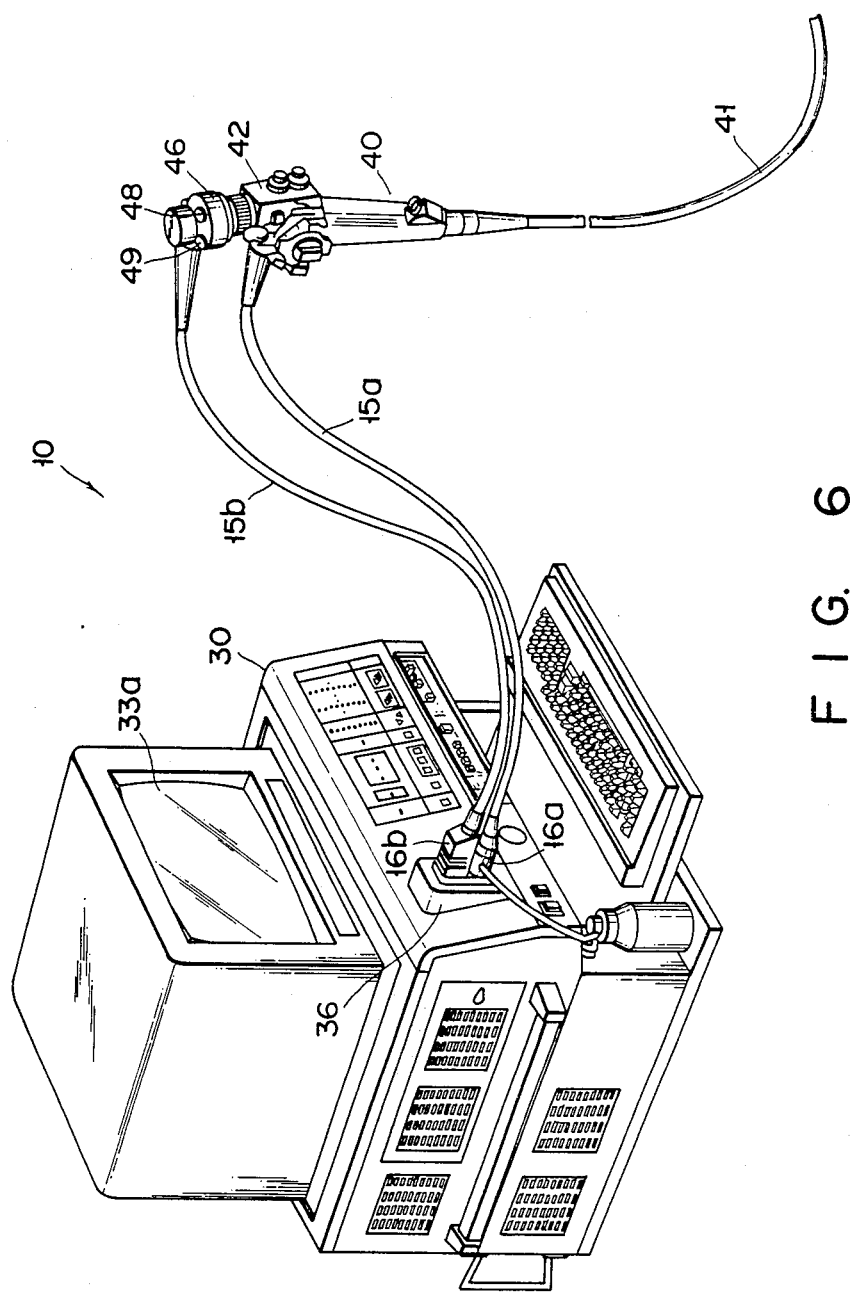
FIG. 6 is a perspective view schematically showing the endoscope system of FIG. 4.

Referring now to FIG. 1, there is schematically shown endoscope system 10 according to an embodiment of the present invention. In this embodiment, system 10 comprises video-signal processing unit 30. Connector or plug 16 of universal cord 15, one end of which is connected to electronic endoscope 20, is coupled to receptacle 36 which is provided on the outer surface portion of unit 30.

Like the conventional ones, endoscope 20 comprises insertion section 21 and handy-control section 22. The one end of universal cord 15 is connected to section 22. The distal end of insertion section 21 contains therein a solid-state image sensing device (not shown), such as a CCD, which converts a field image, formed by an objective optical system (not shown), into an electrical signal. The image sensing device is connected to its corresponding contact of terminal portion 18 of plug 16 by means of a signal cable (not shown), which is passed through insertion section 21, control section 22, and universal cord 15. Endoscope 20 contains a light-guide fiber bundle (not shown) which connects an illumination window (not shown), at the distal end of insertion section 21, and a light guide tube, at terminal portion 18 of plug 16. When plug 16 is coupled to receptacle 36 of video-signal processing unit 30, an illumination light is projected on the fiber bundle.

As shown in FIGS. 1 and 2, handy-control section 22 of endoscope 20 is provided with various remote control switches, such as freeze switch 27, release switch 28, and optical disk switch 29a switch 29. Switches 27, 28 29 and 29a are connected to their corresponding contacts of terminal portion 17 which is passed through universal cord 15.

Besides the remote control switches, angle control knob 23, air-water feed control button 24, and suction control button 25 are arranged at control section 22 of endoscope 20.

As shown in FIG. 3, receptacle 36 of video-signal processing unit 30 is provided with electrical connecting portion 37 and illumination connecting portion 38, which are vertically arranged close to each other. Connecting portions 37 and 38 are connected to terminal portion 17 and 18, respectively, of plug 16 of universal cord 15 when the plug is coupled to receptacle 36.

Electrical connecting portion 37 of receptacle 36 is provided with contactors (not shown) which are individually in touch with the contacts of terminal portion 17 of plug 16 of universal cord 15. Each contactor is connected to its corresponding conventional electric circuit, such as a video-signal processing circuit or a control circuit. Illumination connecting portion 38 of receptacle 36 is connected optically, through lens 32, to conventional light source 31, which is provided in video-signal processing unit 30. Monitor TV 33a for observation, video tape recorder (VTR) 33b, still-image monitor 33c and optical disk 33e are connected to unit 30 by means of cords 34a, 34b 34c and 34e, respectively. TV 33a receives a video signal processed by unit 30. Camera 33d, which is used to record a still image, is controlled by a proper control section in unit 30, with the aid of cord 34d.

Referring now to FIG. 4, there is shown the way of using endoscope 40 for optical inspection. Like the conventional ones, endoscope 40 also comprises insertion section 41 and handy-control section 42. Plug 16a of universal cord 15a, one end of which is connected to control section 42, can be coupled to illumination connecting portion 38 of receptacle 36 of video-signal processing unit 30.

As is generally known, optical endoscope 40 is designed so that an objective optical system, which is located at the distal end of insertion section 41, receives a reflection of a light applied from a suitable light source to a desired portion of the inner wall of the body cavity, through a light guide tube (not shown) which extends through plug 16a, universal cord 15a, and the insertion section. An image of the reflected light is transferred optically to eyepiece portion 43 of handy-control section 42 by means of an image-guide fiber bundle (not shown). The operator can macroscopically observe the condition of the desired wall surface region through eyepiece portion 43, while operating air-water feed control button 44 or suction control button 45 as required.

When observing through a monitor TV, video camera 46 is mounted on eyepiece portion 43 of endoscope 40. This state is indicated by a broken line in FIG. 4.

One end of signal cord 14 is connected to video camera 46. Cord 14 serves to transmit a signal which is produced by a solid-state image sensing device contained in camera 46. Plug 16b is attached to the other end of the signal cord. It can be connected to electrical connecting portion 37 of receptacle 36 of video-signal processing unit 30. Thus, plug 16b is constructed in the same manner as terminal portion 17 of plug 16 of electronic endoscope 20. Individual contacts of plug 16b are adapted to be connected electrically to their corresponding contactors of connecting portion 37 of receptacle 36.

Video camera 46 is provided with remote control switches, including freeze switch 47, release switch 48, and VTR switch 49, which are situated in the same manner as those of control section 22 of electronic endoscope 20.

In the arrangement shown in FIG. 4, plug 16a of universal cord 15a has a shape and size such that it can be connected to illumination connecting portion 38 of receptacle 36, without hindering the connection between plug 16b of signal cord 14 and electrical connecting portion 37.

The operation of endoscope system 10 will now be described.

First, when using electronic endoscope 20, plug 16 of universal cord 15 is coupled to receptacle 36 of video-signal processing unit 30 by insertion. Insertion section 21 is inserted into the body cavity for monitoring. In this state, the operator can start freezed-picture observation, still-photographing by means of a still-image recorder including monitor 33c and camera 33d, and image recording by means of video tape recorder 33b and optical disk 33e, by operating freeze switch 27, release switch 28, VTR switch 29 and optical disk switch 29a, respectively. Thus, the operator can perform these operations easily at hand. This may also be done by operating control switches of the same functions on the side of processing unit 30, depending on the working conditions.

When using optical endoscope 40 fitted with video camera 46, as shown in FIG. 6, plug 16a of universal cord 15a of endoscope 40 is coupled to illumination connecting portion 38 of receptacle 36 of video-signal processing unit 30. Also, plug 16b of signal cord 14, which is connected to camera 46, is coupled to electrical connecting portion 37 of receptacle 36. As a result, a video signal, produced by the solid-state image sensing device in the video camera, which is mounted on eyepiece portion 43 of endoscope 40, is guided to processing unit 30.

Thus, observation through monitor TV 33a can be made also with use of optical endoscope 40. Like endoscope 20, video camera 46 is provided with the remote control switches, including freeze switch 47, release switch 48, VTR switch 49 and optical disk switch 49a. Therefore, the operator can start the freezed-picture observation, still-photographing, and image recording by operating the control switches as required. Namely, the operator can perform these operations at hand, while operating endoscope 40.

Accordingly, the operator need not operate the control switches on the side of video-signal processing unit 30. Thus, he can perform an accurate switching operation easily and quickly. Since the remote control switches on the two sides are arranged correspondingly, moreover, endoscopes of either type can be used compatibly with one and the same video-signal processing unit.

Figure 7:
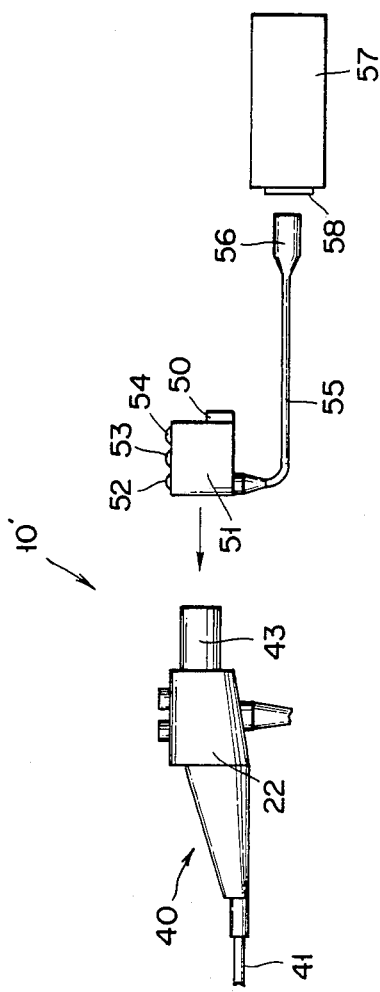
FIG. 7 schematically shows another embodiment of the invention using a video camera with a viewfinder.

FIG. 7 shows endoscope system 10' according to a second embodiment of the present invention.

The system of this embodiment uses video camera 51 with viewfinder 50 thereon. Camera 51 is also provided with various remote control switches, including freeze switch 52, release switch 53, and VTR switch 54, which are situated in the same manner as those of endoscope 20. Plug 56 of signal cord 5 of camera 51 has the same construction as plug 16b of the first embodiment. It is adapted to be connected to connector socket 58 of video-signal processing unit 57.

Video camera 51 of this embodiment is also provided with various remote control switches which are situated in the same manner as those of the first embodiment. Therefore, the operator can operate these switches easily at hand, just as in operating their counterparts of endoscope 20, with the same results.

Thus, according to the present invention, if a video camera is used with an optical endoscope, in a manner such that it is mounted on the eyepiece portion of the endoscope, the operator can operate remote control switches on the camera. In other words, the operator himself can operate the switches at the handy-control section of the optical endoscope, just as in operating the electronic endoscope. In consequence, he can perform an accurate switching operation easily and quickly, without regard to the type of endoscope used.

Although a video tape recorder is used for image recording in the illustrative embodiments described herein, it is to be understood by one skilled in the art that an optical disk unit may also be used as the recorder.

What is claimed is:

1. In an endoscope system which comprises an endoscope including a handy-control section and an insertion section adapted to be inserted into the body cavity, and a video-signal processing unit including an electric circuit capable of receiving and processing a video signal, produced by a solid-state image sensing device, through the medium of the endoscope, and of recording and/or displaying the video signal on a monitor TV, the improvement which comprises:

a receptacle provided on the outer surface of the video-signal processing unit, said receptacle including an electrical connecting portion connected to the electric circuit in the video-signal processing unit;

said endoscope being one of an optical endoscope and an electronic endoscope;

said optical endoscope having an eyepiece portion at a control portion thereof; a video camera having the solid-state image sensing device therein and mounted on said eyepiece portion for optical observation at the control section of the optical endoscope, said video camera being connected to a first signal cord having a plug connectable with the electrical connecting portion of the receptacle, and said video camera further having a remote control switch means for controlling the video-signal processing unit through the medium of the first signal cord;

said electronic endoscope having a first universal cord with one end connected to said electronic endoscope and its other end having a plug connectable to the electrical connecting portion of the receptacle alternately with the first signal cord plug, said endoscope having a solid-state image sensing device contained in the distal end of an insertion section thereof, and remote control switch means mounted on a handy-control section thereof for controlling the video-signal processing unit, said first universal cord having a second signal cord and a light guide tube therein.

2. The endoscope system according to claim 1, wherein said receptacle is provided with an illumination connecting portion situated close to the electrical connecting portion and connected optically to an illumination light source, said illumination connecting portion being connectable with a plug of a second universal cord containing a light guide tube therein, one end of said second universal cord being connected to the handy-control section of the optical endoscope including an eyepiece portion for macroscopic observation of the endoscope.

3. The endoscope system according to claim 1, wherein said receptacle of the video-signal processing unit can be coupled with a plug of a third signal cord of a video camera with a viewfinder, said camera having remote control switches capable of being used to control the video-signal processing unit.

4. The endoscope system according to claim 1, wherein a video tape recorder and a still-image recorder are connected to said video-signal processing unit, and said remote control switches for the video-signal processing unit, mounted on the handy-control section, include a freeze switch, a release switch, and a VTR switch.

5. The endoscope system according to claim 1, wherein a video tape recorder and a still-image recorder are connected to said video-signal processing unit, and said remote control switches for the video-signal processing unit, mounted on the video camera, include a freeze switch, a release switch, and a VTR switch, said switches being situated in the same positions as their counterparts of an electronic endoscope.

6. The endoscope system according to claim 4, wherein said video-signal processing unit includes a video tape recorder and a still-image recorder, and said remote control switches for the video-signal processing unit, mounted on the video camera with the viewfinder, include a freeze switch, a release switch, and a VTR switch, said switches performing the same functions as their counterparts of an electronic endoscope.

7. The endoscope system according to claim 5, wherein said recorder is an optical disk unit.

8. The endoscope system according to claim 6, wherein said recorder is an optical disk unit.

9. The endoscope system according to claim 7, wherein said recorder is an optical disk unit.

* * * * *